United States Patent
Willers et al.

(10) Patent No.: US 11,000,349 B2
(45) Date of Patent: May 11, 2021

(54) METHOD, SYSTEM AND COMPUTER READABLE STORAGE MEDIA FOR DETERMINING ARTICULATION PARAMETERS

(71) Applicant: DENTSPLY SIRONA Inc., York, PA (US)

(72) Inventors: Nadine Willers, Darmstadt (DE); André Koza, Lorsch (DE)

(73) Assignee: DENTSPLY SIRONA Inc., York, PA (US)

( * ) Notice: Subject to any disclaimer, the term of this patent is extended or adjusted under 35 U.S.C. 154(b) by 64 days.

(21) Appl. No.: 16/431,830

(22) Filed: Jun. 5, 2019

(65) Prior Publication Data

US 2020/0383752 A1 Dec. 10, 2020

(51) Int. Cl.
| | |
|---|---|
| *A61C 7/00* | (2006.01) |
| *G16H 30/40* | (2018.01) |
| *A61B 5/00* | (2006.01) |
| *G06N 3/08* | (2006.01) |
| *G06T 7/00* | (2017.01) |
| *G06T 17/00* | (2006.01) |

(52) U.S. Cl.
CPC ............ *A61C 7/002* (2013.01); *A61B 5/0077* (2013.01); *G06N 3/08* (2013.01); *G06T 7/0014* (2013.01); *G06T 17/00* (2013.01); *G16H 30/40* (2018.01); *G06T 2200/08* (2013.01); *G06T 2207/10004* (2013.01); *G06T 2207/30036* (2013.01); *G06T 2210/41* (2013.01)

(58) Field of Classification Search
CPC ......... A61C 7/002; A61C 7/00; A61C 9/0046; A61C 7/08; A61C 7/146; A61C 13/0004; A61C 9/0053; G06T 17/00; G06T 17/20; G06T 2207/30036
See application file for complete search history.

(56) References Cited

U.S. PATENT DOCUMENTS

| | | | |
|---|---|---|---|
| 8,706,672 B2 | 4/2014 | Malfliet | |
| 9,336,336 B2 | 5/2016 | Deichmann | |
| 9,642,686 B1 | 5/2017 | Kalman | |
| 2007/0238065 A1* | 10/2007 | Sherwood | A61C 7/08 433/24 |
| 2008/0176182 A1 | 7/2008 | Hultgren | |

(Continued)

FOREIGN PATENT DOCUMENTS

| | | |
|---|---|---|
| EP | 3453333 A1 | 3/2019 |
| WO | 201367606 A2 | 5/2013 |

OTHER PUBLICATIONS

International Search Report; PCT/US2020/036230; Aug. 14, 2020(completed); dated Aug. 28, 2020.

(Continued)

*Primary Examiner* — Ross Varndell
(74) *Attorney, Agent, or Firm* — Dentsply Sirona Inc.

(57) ABSTRACT

A method, system and computer readable storage media for determining articulator parameters. A dentist may use a mobile device such as a smart phone to quickly and inexpensively visualize a 3D model of a patient's face and jaw, with a depth sensor being used to detect depth information. Articulator parameters may then be obtained to be used for treatment planning based on an analysis of the correct functioning of the patient's teeth.

15 Claims, 11 Drawing Sheets

(56) References Cited

U.S. PATENT DOCUMENTS

| | | | |
|---|---|---|---|
| 2012/0107763 A1* | 5/2012 | Adams | A61B 1/24 433/29 |
| 2013/0151208 A1* | 6/2013 | Ito | A61C 11/00 703/1 |
| 2013/0204600 A1* | 8/2013 | Mehra | G16H 50/50 703/11 |
| 2018/0110603 A1* | 4/2018 | Stipek, Sr. | A61C 11/08 |
| 2018/0263731 A1* | 9/2018 | Pokotilov | G06T 17/20 |
| 2018/0263733 A1 | 9/2018 | Pokotilov | |
| 2019/0216580 A1* | 7/2019 | Fisker | A61C 11/00 |
| 2019/0290408 A1* | 9/2019 | Fisker | A61C 13/0004 |

OTHER PUBLICATIONS

Written Opinion of the International Searching Authority; PCT/US2020/036230; Aug. 14, 2020(completed); dated Aug. 28, 2020.

\* cited by examiner

METHOD, SYSTEM AND COMPUTER READABLE STORAGE MEDIA FOR DETERMINING ARTICULATION PARAMETERS

FIELD OF THE INVENTION

The present application relates generally to a method, a system and computer readable storage media for determining articulation parameters and, more particularly, to a method, system and computer readable storage media for utilizing 3D face detection methods to determine articulation parameters of a patient.

BACKGROUND OF THE INVENTION

Dentists may use articulators having upper and lower components to which maxillary and mandibular casts may be attached to reproduce the static relationship of a patient's maxilla to the patient's mandible. This may be used to study individual teeth and full dental arches for diagnosis and/or treatment planning as well as to allow the adjustment of fixed and removable prostheses and dental restorations.

A facebow may be used to set up an articulator wherein a determination of the movements of the patient's temporomandibular joint may be carried out. Herein, the facebow may be positioned in the ears to transfer an arbitrary hinge axis location by referencing an approximation using the patient's ears. The facebow may also be aligned to the face of the patient with a mouth piece. A fixed frame carrying adjustable pivot joints may be used for supporting the facebow; along with positively driven positioning mechanisms for adjusting the pivot joints to provide a desired position and aspect of the facebow.

The facebow may transfer the relationship between the maxillary arch and temporomandibular joint to a cast. It may record the maxilla's relationship to the External Acoustic Meatus, in a hinge axis and aid in mounting a maxillary cast on the articulator.

The patient may also perform various chewing movements (lateral, forward/backward movements of the jaw etc.), allowing the dentist to read certain values on the facebow for use in for example a commercial articulator.

This requires a lot of time and presents an unpleasant procedure for the patient. It would therefore be useful to quickly and automatically determine articulation parameters without the use of a physical facebow or physical articulator.

U.S. Pat. No. 9,336,336B2 discloses using face detection for "smile" design applications. Herein, a dental restoration may be designed for a patient, by providing one or more 2D images, with at least one 2D image including at least one facial feature; providing a 3D virtual model of a part of the patient's oral cavity and arranging one of the 2D images relative to the 3D virtual model. The 3D virtual model and the 2D image are both visualized in the 3D space; and a restoration is modelled on the 3D virtual model such that it fits the facial feature of the at least one 2D image.

U.S. Pat. No. 9,642,686B1 discloses a method and a system for recording characteristics of an occlusal arch of a patient using a portable computing device. Herein, a virtual facebow may be used to record characteristics of an occlusal arch of a patient using a facial alignment image having a set of crosshairs. The recorded characteristics may then be used to replicate the alignment of the patient's occlusal arch with a maxillary cast in a lab stand, and the maxillary cast may then be moved to an articulator for the production of customized dental prosthetics for the patient.

PCT Application No. WO201367606 discloses using digital elements to articulate a model into a physical articulator wherein a physical study model is arranged in an articulator and a direction of a canine line and the occlusion plane are determined on the study model.

U.S. Pat. No. 8,706,672B2 discloses a computer assisted method of creating a custom tooth using facial analysis comprising obtaining data about an area which is to be treated and data about a face of a patient, performing an analysis of the data to determine properties of at least the face of the patient and creating a modified tooth set-up using a set of stored rules which make use of the determined facial properties.

These methods either do not utilize depth information or employ the use of x-ray images which may not be ideal.

SUMMARY OF THE INVENTION

Existing limitations associated with the foregoing, as well as other limitations, can be overcome by a method, system and computer readable storage media for determining articulation parameters.

In an aspect herein, the present invention may provide a method for determining articulation parameters, the method comprising: receiving images of a patient's face; determining fixed and/or moving points in the patient's face based on the received images, calculating the articulator parameters based on the determined fixed and/or moving points.

In another aspect herein, the method may further comprise one or more of the following steps: (i) wherein the articulator parameters are chosen from the group consisting of (1) Sides of a Bonwill triangle, (2) Intercondylar distance, (3) Balkwill angle, (4) Sagittal condylar path inclination, (5) Bennett angle, (6) Initial Bennett movement and (7) Curve of Spee, (ii) further comprising reconstructing a 3D model of a face of the patient from the received images, (iii) further comprising superimposing a scan of the intraoral cavity of the patient on the 3D model, (iv) wherein the determining step is achieved by feature analysis (v), wherein the feature analysis includes the use of deep learning to determine fixed and/or moving points, (vi) wherein the fixed points include a location of a temporomandibular joint. (vii) wherein the calculating step is achieved using geometrical distances and/or angles measured using the fixed and/or moving points, (viii) further comprising using the calculated articulator parameters to fill a virtual articulator with articulation values, (ix) further comprising analyzing the functioning of teeth based on the articulator parameters, (x) further comprising producing a restoration or a treatment plan based on the articulator parameters.

In yet another aspect, the present invention may provide a computer implemented method for determining articulation parameters, the computer-implemented method comprising: training, using one or more computing devices and a plurality of training images, a deep neural network to map one or more fixed and/or moving points in at least one portion of each training image to one or more highest location probability values of a location probability vector; receiving, by the one or more computing devices, images of a patient's face including at least one jaw; identifying, using the trained neural network, fixed and/or moving points based on one or more output location probability values of the deep neural network, and calculating the articulator parameters based on the determined fixed and/or moving points.

In another aspect herein, the computer implemented method may further provide a method wherein the deep neural network is a convolutional neural network.

In yet another aspect herein, a system may be provided for determining articulation parameters, the system comprising at least one processor configured to perform the steps of: receiving images of a patient's face; determining fixed and/or moving points in the patient's face based on the received images, and calculating the articulator parameters based on the determined fixed and/or moving points.

The system may also provide one or more combinations of the following: (i) wherein the processor is further configured to choose the articulator parameters from the group consisting of (1) Sides of a Bonwill triangle, (2) Intercondylar distance, (3) Balkwill angle, (4) Sagittal condylar path inclination, (5) Bennett angle, (6) Initial Bennett movement and (7) Curve of Spee, (ii) wherein the processor is further configured to reconstruct a 3D model of a face of the patient from the received images, (iii) wherein the processor is further configured to superimpose a scan of the intraoral cavity of the patient on the 3D model, (iv) wherein the processor is further configured to determine the fixed and/or moving points by feature analysis, (v) wherein the feature analysis includes the use of deep learning to determine fixed and/or moving points, (vi) wherein the fixed points include a location of a temporomandibular joint, (vii) wherein the processor is further configured to produce a restoration or a treatment plan based on the articulator parameters.

In even yet another aspect of the present invention, a non-transitory computer-readable storage medium may be provided for storing a program which, when executed by a computer system, causes the computer system to perform a procedure comprising: receiving images of a patient's face; determining fixed and/or moving points in the patient's face based on the received images, and calculating the articulator parameters based on the determined fixed and/or moving points.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Figure 1:
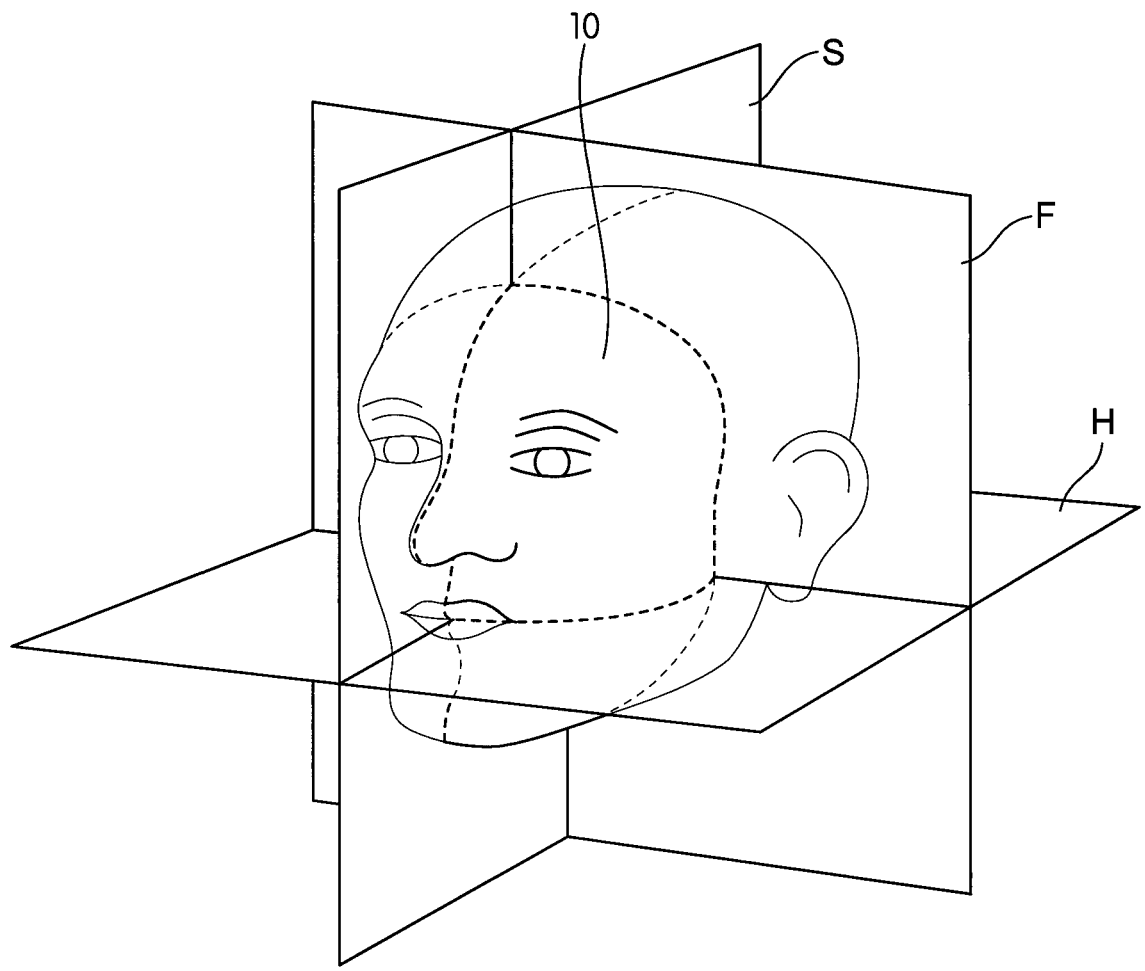
FIG. 1 is a perspective view of a face of a patient illustrating its relationship with three planes of space.

Different ones of the figures may have at least some reference numerals that may be the same in order to identify the same components, although a detailed description of each such component may not be provided below with respect to each Figure.

DETAILED DESCRIPTION OF THE INVENTION

In accordance with example aspects described herein, a method, system and computer readable storage media may be provided for determining articulation parameters.

Method for Determining Articulation Parameters

Determining the articulation parameters of a specified patient such as intercondylar distance and Bennett angle is essential for the production of a restoration. Various articulation parameters, described in more detail hereinafter, provide important information about the natural and correct process of jaw movement during the chewing process. The information obtained allows a correct articulation of the jaws as well as an indication of the cusp and groove positions in teeth. This saves the dentist and patient time and inconvenience due to later adaptions of restorations.

A goal of the invention is to relate parts of a patient's oral cavity such as the maxillary arch, mandibular arch and/or temporomandibular joint to the face in planes of space through the use of images taken with a depth sensor. This may be done for dentofacial analysis of the maxillary arch as well as for the establishment of functional relationships with the mandibular arch. The process of determining the articulation parameters may be digitized through the use of images taken with a depth sensor, thereby, removing the need for complex structures such as a physical facebow.

FIG. 1 illustrates imaginary planes passing through a 3D reconstruction of a patient's face 10 that preferably includes the jaws, the planes being sagittal plane S, a frontal plane F, and a horizontal plane H. The sagittal plane S is an anatomical plane that may divide the patient's head into two parts. Thus, the sagittal plane that divides the head into two halves is a mid-sagittal plane. The frontal plane F may be at right angles with the sagittal plane S, and may divide the head into anterior and posterior regions. The horizontal plane H may also be at right angles to the sagittal plane and may divide the head into upper and lower regions.

A virtual articulator may enable a dentist to configure a restoration and/or examine the functioning of teeth, based on for example determined locations of virtual contact points between upper and lower jaws of the patient's oral cavity. It may also enable an orthodontist to among other things, detect collisions between teeth as the teeth are moved/shifted, therefore allowing the detection of a difference between a normal bite situation before any movements are carried out and the bite situation after movement. In order to configure the virtual articulator, patient specific inputs (patient specific articulation parameters) may be obtained from images of the patient's head, said images containing geometric information that may be used to determine relative distances between parts of the patient's dentition from each other as well as from the temporomandibular joint.

Said articulation parameters may include but may not be limited to (i) Sides 11a of the Bonwill triangle 11 (arms), (ii) Intercondylar distance 15 (base of the Bonwill triangle), (iii) Balkwill angle 17, (iv) Sagittal condylar path inclination β, (v) Bennett angle α, (vi) Initial Bennett movement (Immediate side shift left/right), (vii) Curve of Spee 18. These parameters may be determined by tracking fixed points 20 and/or moving points 21 on the patient's face using a camera system 22 having a depth sensor 24 and determining geometrical distances and angles between these points and specified parts of the patient's dentition as described hereinafter.

Figure 2:
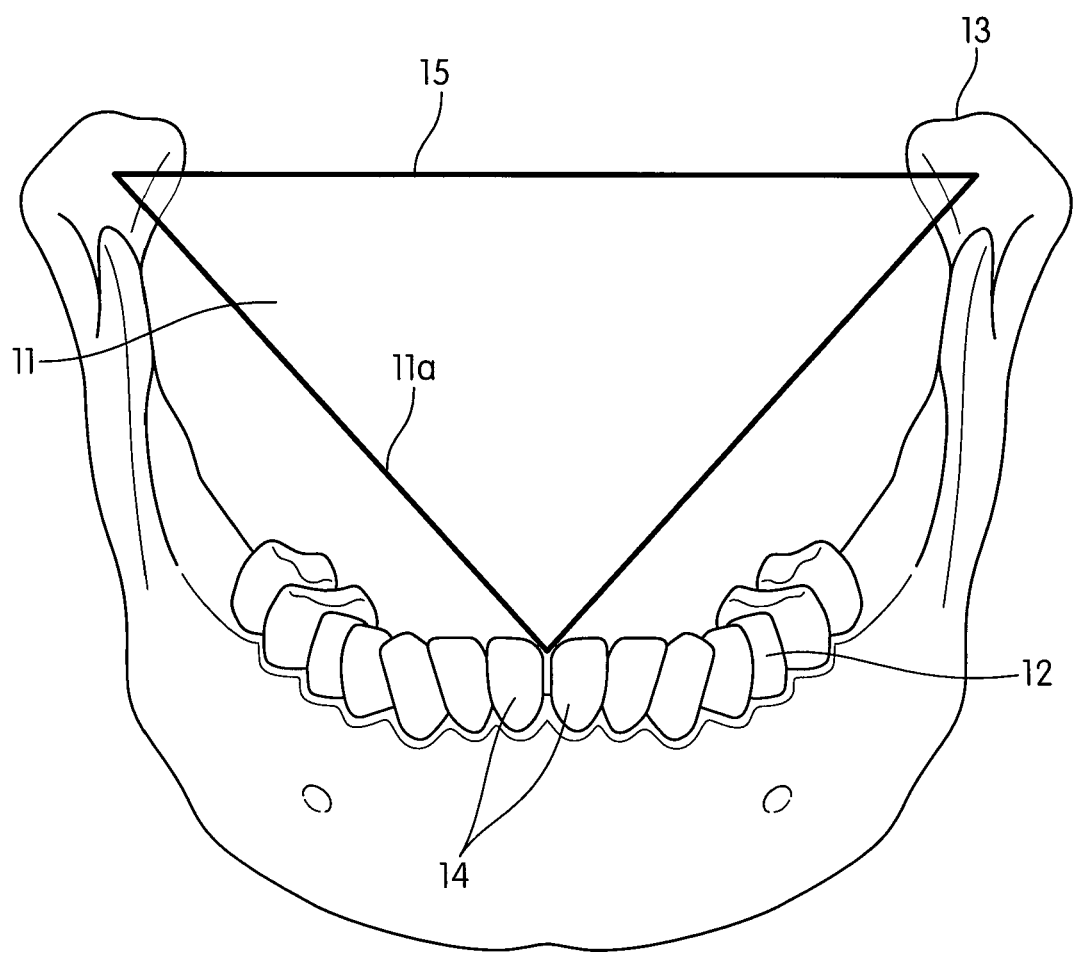
FIG. 2 is a perspective view of a jaw illustrating a Bonwill triangle according to an exemplary embodiment of the present invention.

FIG. 2 illustrates the Bonwill triangle 11 which is an equilateral triangle connecting the contact points of the mandibular central incisors' 14 incisal edge (or the midline of the mandibular residual ridge) to the midpoint of each condyle 13, and from one condyle 13 to the other 13. Since it is an equilateral triangle, the length of the sides 11a may be approximately equal (usually 4 inches). Knowing the location or approximate location of the right and left temporomandibular joints 23 based on anatomical feature extraction methods discussed herein, the sides of the Bonwill triangle 11 may be computed.

Figure 3A:
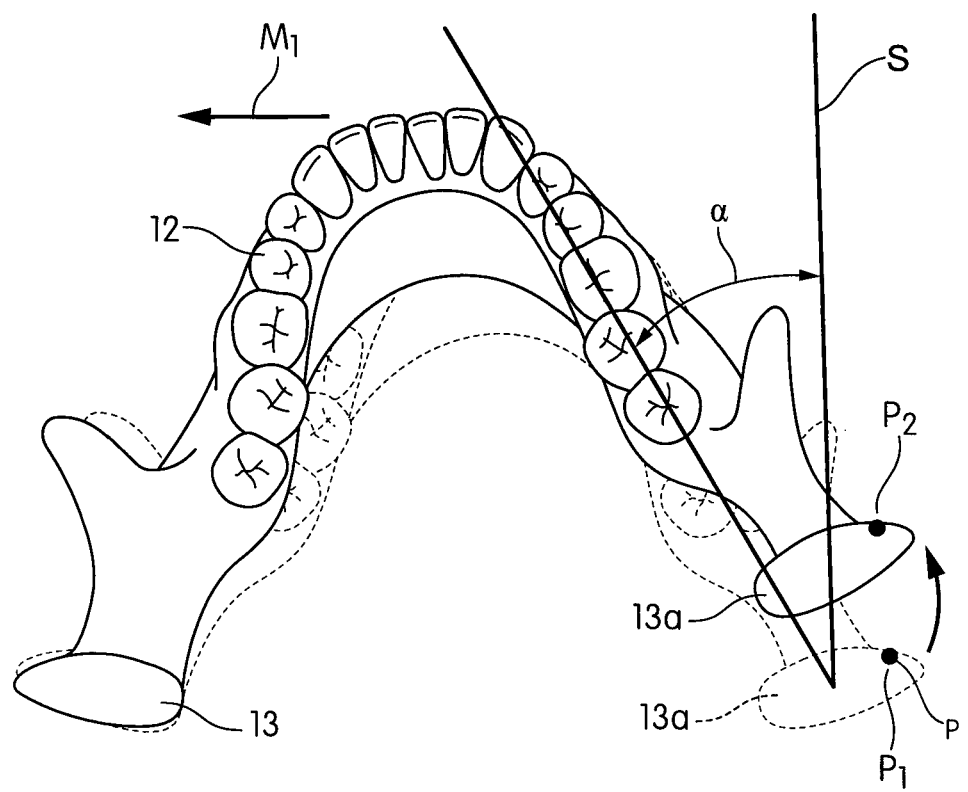
FIG. 3a is a perspective view of a jaw illustrating a Bennett angle according to an exemplary embodiment of the present invention.
Figure 3B:
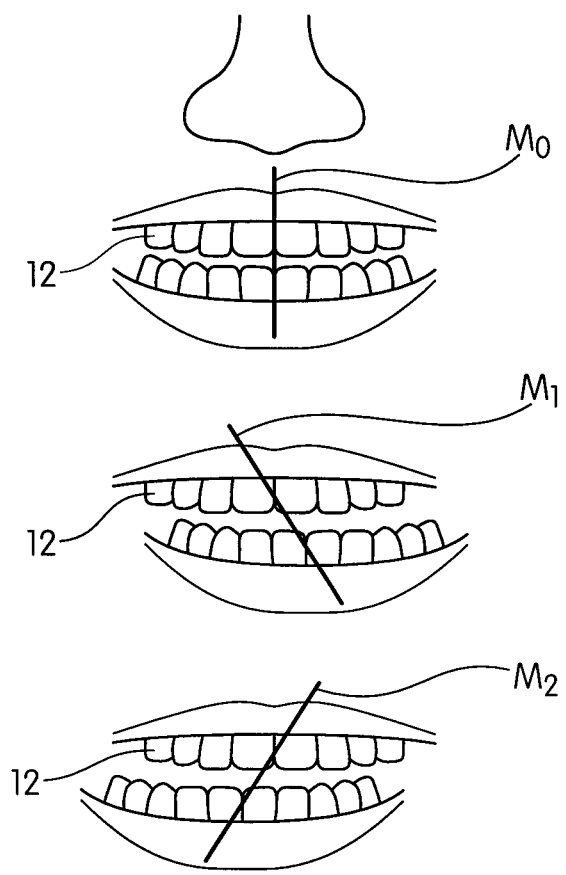
FIG. 3b is a sketch illustrating movements of a patient's oral cavity and lips according to an exemplary embodiment of the present invention.

FIG. 3a illustrates the Bennett angle α, which is the angle formed between the sagittal plane S and a path of the advancing condyle 13, as the mandible moves laterally, when viewed on a horizontal plane H. As shown in FIGS. 3a and 3b, as the mandible moves to the left ($M_1$), from a an initial position ($M_0$), an angle α is formed between the plane S and the path of the advancing condyle 13a, and point p on condyle 13a moves from position $P_1$ to position $P_2$. Initial Bennett movement (also known as Immediate side shift) refers to a movement in which both condyles may be displaced to the side at the start of lateral movement of the mandible; i.e., the whole mandible may perform a sideways movement running parallel to the hinge axis before the nonworking condyle moves forward, downward, and inward. This side shift may be performed with difficulty as an isolated movement, and it may be interpreted as evidence of joint damage, e.g. capsule or ligament strain.

Figure 4:
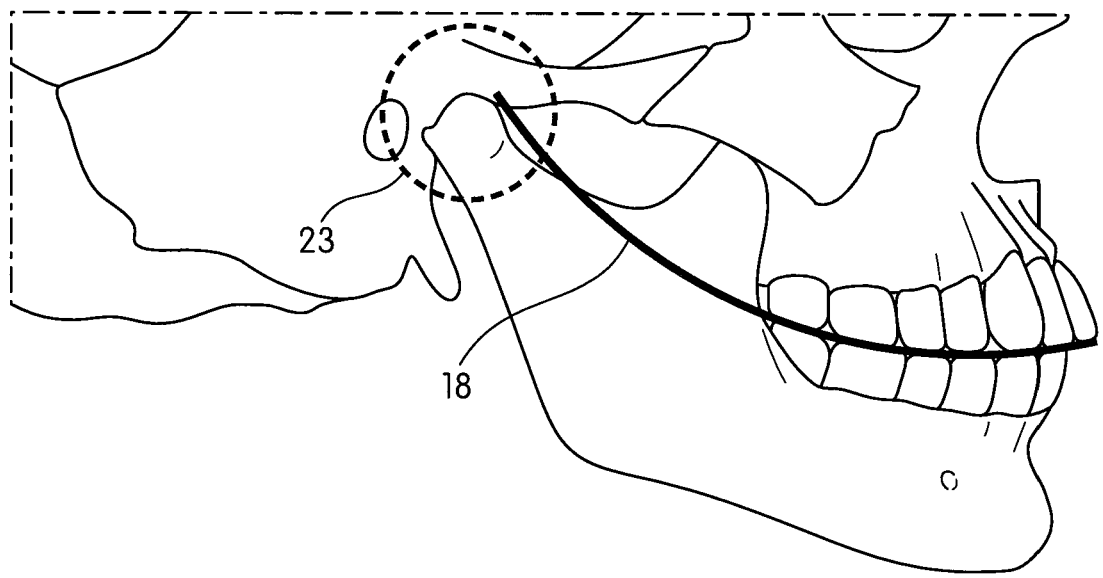
FIG. 4 is a side view of a jaw showing a curve of Spee according to an exemplary embodiment of the present invention.

FIG. 4 shows the curve of Spee, which is a curvature of the mandibular occlusal plane beginning at the premolar and following the buccal cusps of the posterior teeth, continuing to the terminal molar.

Figure 5:
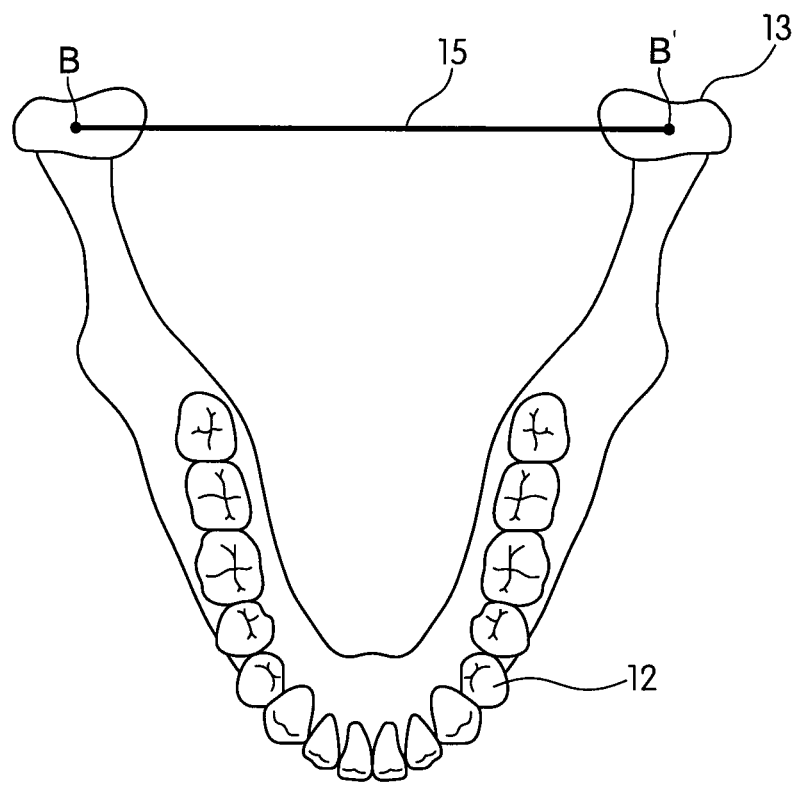
FIG. 5 is a top view of a jaw showing an intercondylar distance according to an exemplary embodiment of the present invention.
Figure 6:
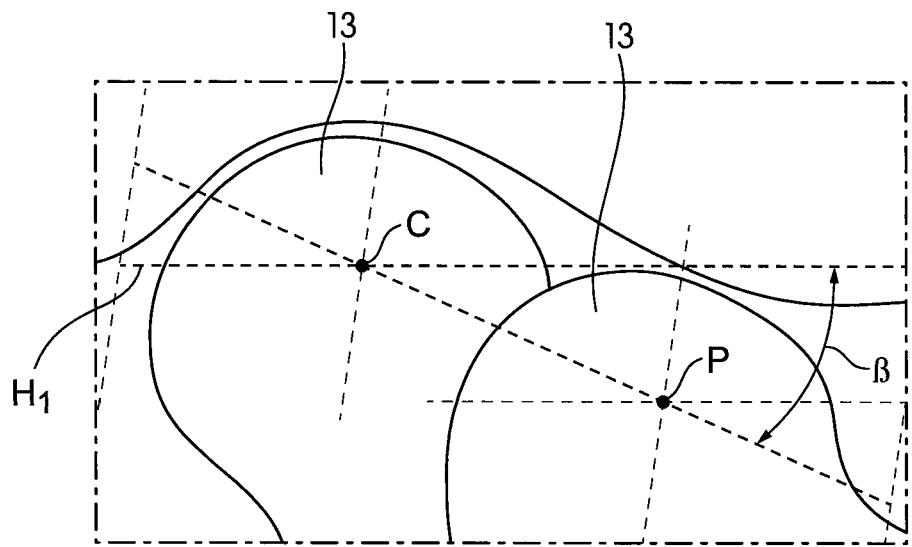
FIG. 6 is a side view of a jaw showing a sagittal condylar path inclination according to an embodiment of the present invention.

FIG. 5 illustrates the intercondylar distance 15 which is a distance between the two temporomandibular joints 23 of a patient (i.e. the distance between the condyles 13). FIG. 6 is a diagram showing the sagittal condylar path inclination Π, the angle formed by the condylar path (path P-C, followed by the condyle 13 in the temporomandibular joint 23) and the horizontal reference plan Hi. This may occur during protrusion (forward movement) of the mandible of the patient.

Figure 7:
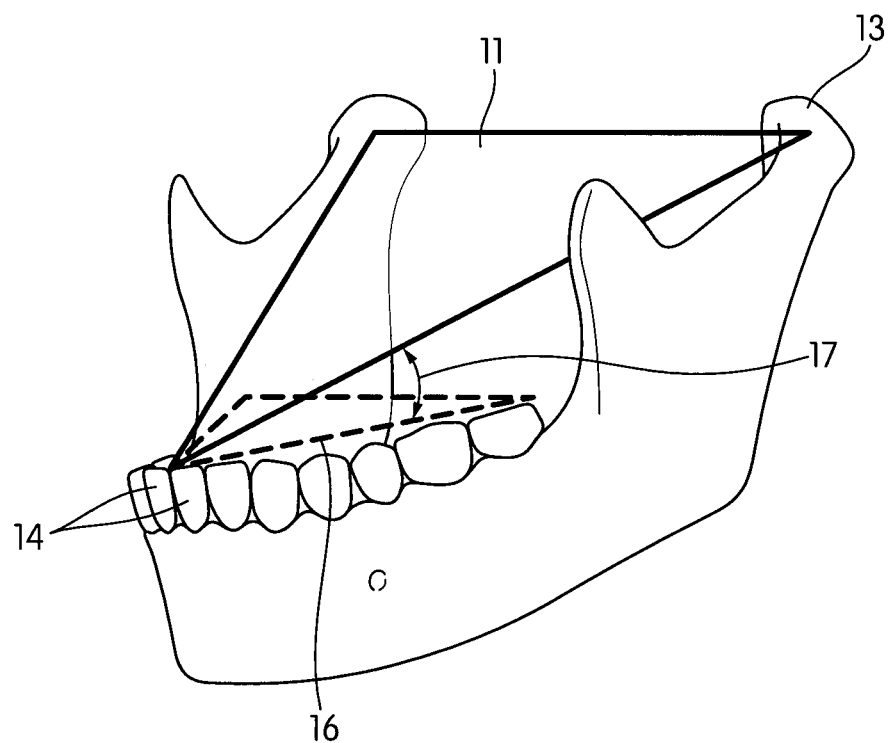
FIG. 7 is a perspective view of a jaw illustrating a Balkwill angle according to an exemplary embodiment of the present invention.

FIG. 7 shows the Balkwill angle 17 which is an angle between by the Bonwill triangle 11 and the Balkwill triangle/occlusal triangle 16 defined by the horizontal plane of the dentition of the mandible. Knowing these and other similar parameters for a virtual articulator without the use of a physical facebow or physical articulator may help reduce treatment times in a dentist's office.

Figure 8:
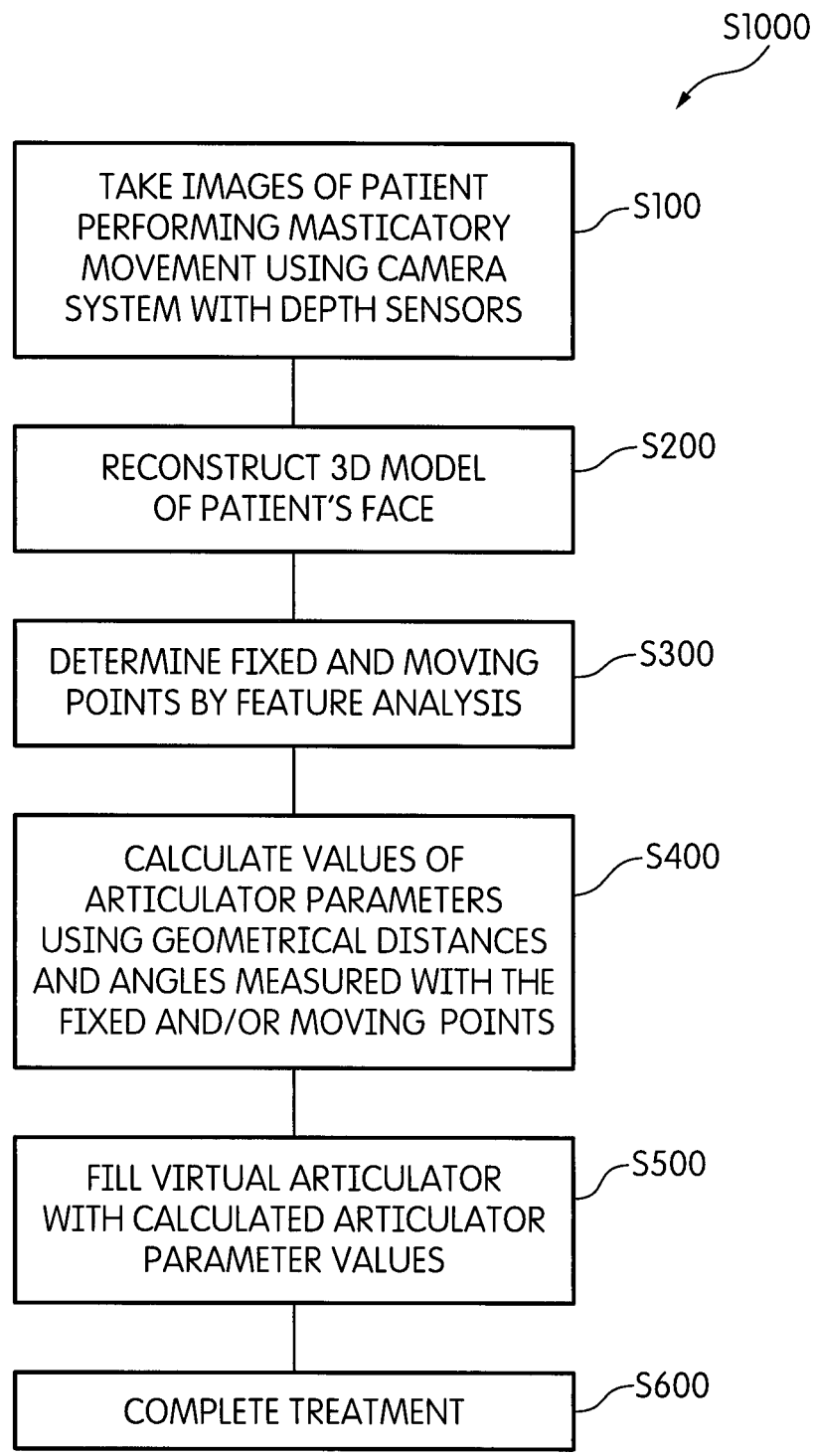
FIG. 8 is a flow chart describing a method according to an exemplary embodiment of the present invention.
Figure 9:
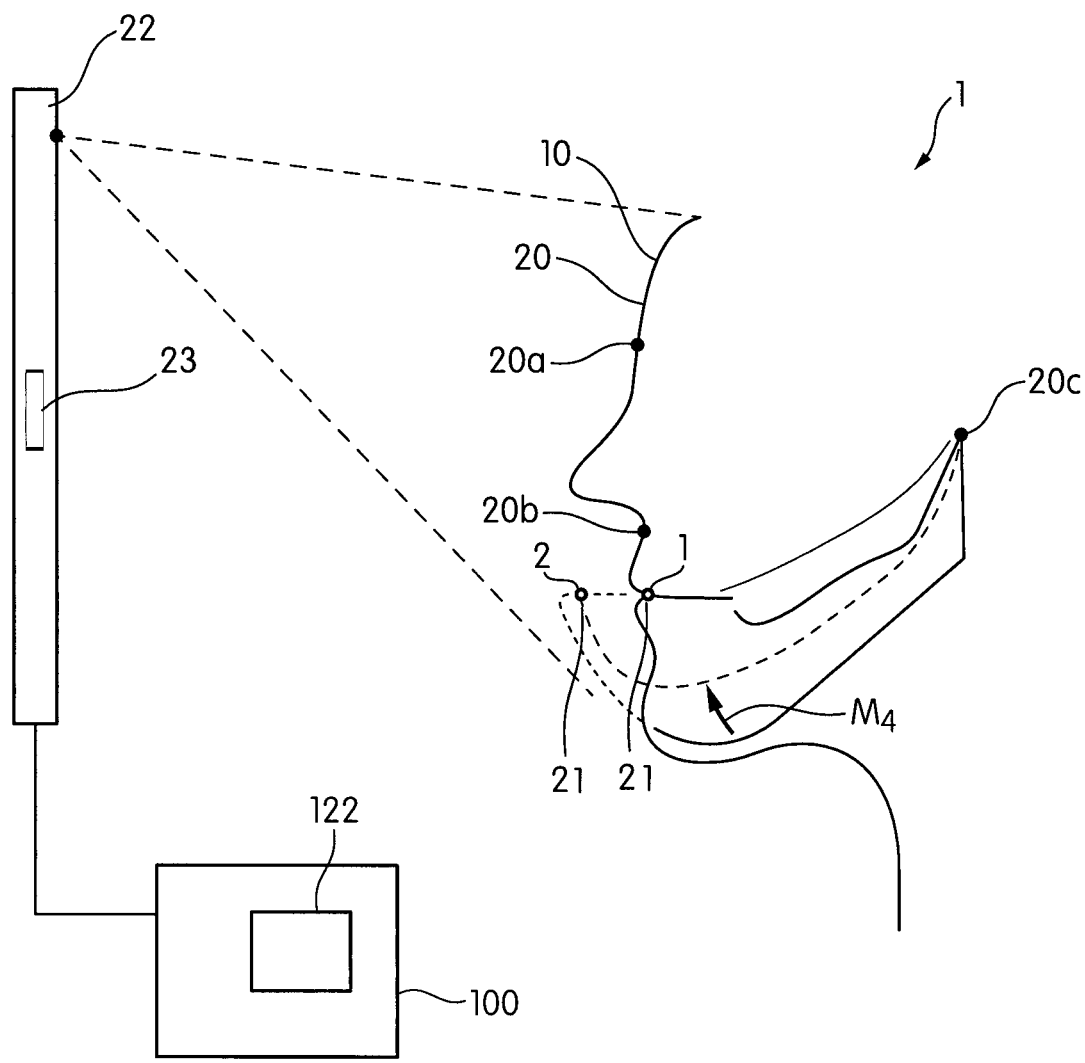
FIG. 9 is a side view of a system illustrating fixed and moving points according to an exemplary embodiment of the present invention.

Having described the exemplary articulator parameters, reference will now be made to FIGS. 8-10, to illustrate a process S1000 that may be employed in accordance with at least some of the example embodiments herein. Process S1000 may begin at Step S100 wherein a plurality images of a patient performing predetermined masticatory/chewing movements may be taken. The images may be taken using a camera system 22 having a depth sensor 24. For example, using a smartphone with depth sensors (such as the Lenovo Phab 2 Pro with Google Tango technology) or a stand-alone combination of color and depth cameras, the patient's face may be captured. The depth information may be used to reconstruct a 3D model of the face 10, including the jaws, as shown in Step S200. Moreover, a series of 2D images may be captured while the patient performs the predetermined masticatory movements and corresponding 3D models of the face 10 may be reconstructed for each movement. The reconstruction may be done in real time or may be done when necessary and used for measurements. Alternatively, knowing how 2D images relate to each other with respect to position as well as their scale, distances and angles, those images may be calculated without doing a 3D reconstruction. In addition, movements may be recorded and/or tracked by identifying relevant points and comparing them frame to frame. The images/recordings may be saved in a database. In an exemplary embodiment, the images may be saved and tagged in the database for specific articulation positions. The movements may include shoving the lower jaw (mandibular arch) in front of upper jaw (maxillary arch) and moving the lower jaw left and right while upper jaw is in contact with the lower jaw. The movements may be determined to correspond to the natural movements of the patient which chewing as well as movements that may allow the collection of geometrical distances and angles needed for articulation.

In Step S300, fixed points 20 and/or moving points 21 may be determined by feature analysis. This may include the use of natural markers of the dental and facial anatomy preferably without the use of predetermined artificial markers. However, in some embodiments, predetermined artificial markers may be placed on predetermined positions on the face and/or oral cavity and the fixed points 20 and/or moving points may be determined by recognition of the predetermined artificial markers. These fixed points 20 and/or moving points 21 may be determined to aid in the calculation of various distances and angles. Fixed points 20 may help in determining the orientation of the face during movement. The fixed points 20 and/or moving points 21 may preferably be points on the face or oral cavity containing little or no soft tissue such as, for example, on the forehead 20a, under the nose, 20b, and those points on either side of the head 20c where the temporomandibular joint 23 is anchored and from which the movement originates. Some moving points 21 however may contain soft tissue (e.g. the lips).

Other natural markers may include bumps, fissures, position of the teeth and their relation to each other artificial markers may include stickers, color dots with a pen, glued-on geometries and the like.

Figure 10A:
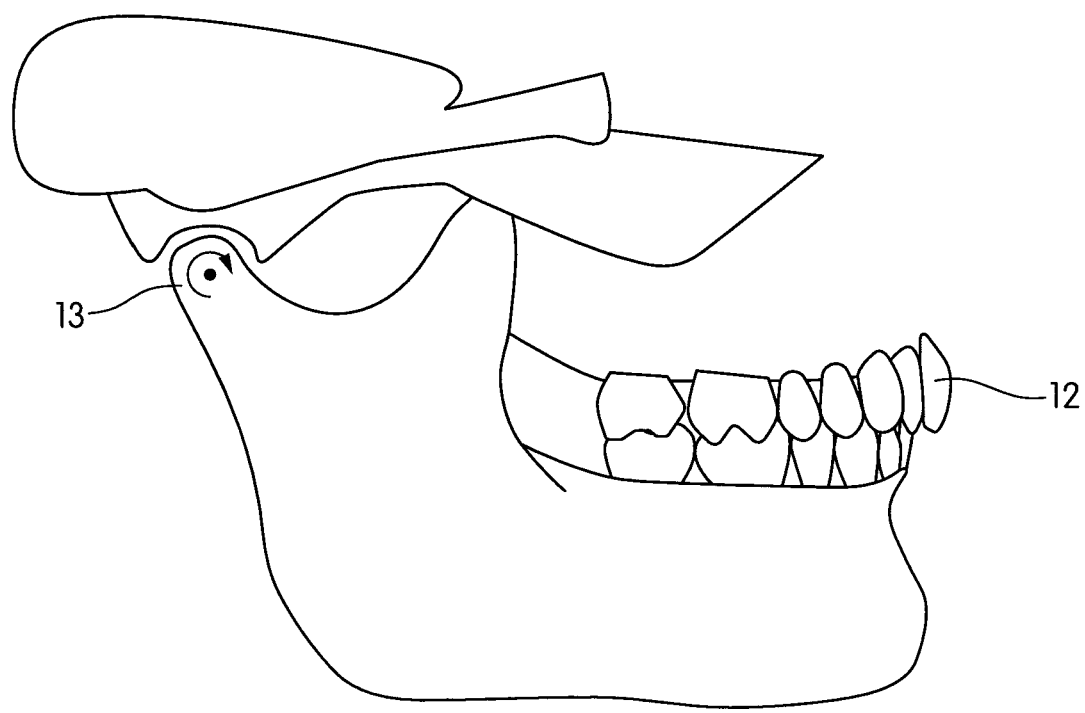
FIG. 10a is a side view of a jaw illustrating a first movement of a patient's oral cavity according to an exemplary embodiment of the present invention.
Figure 10B:
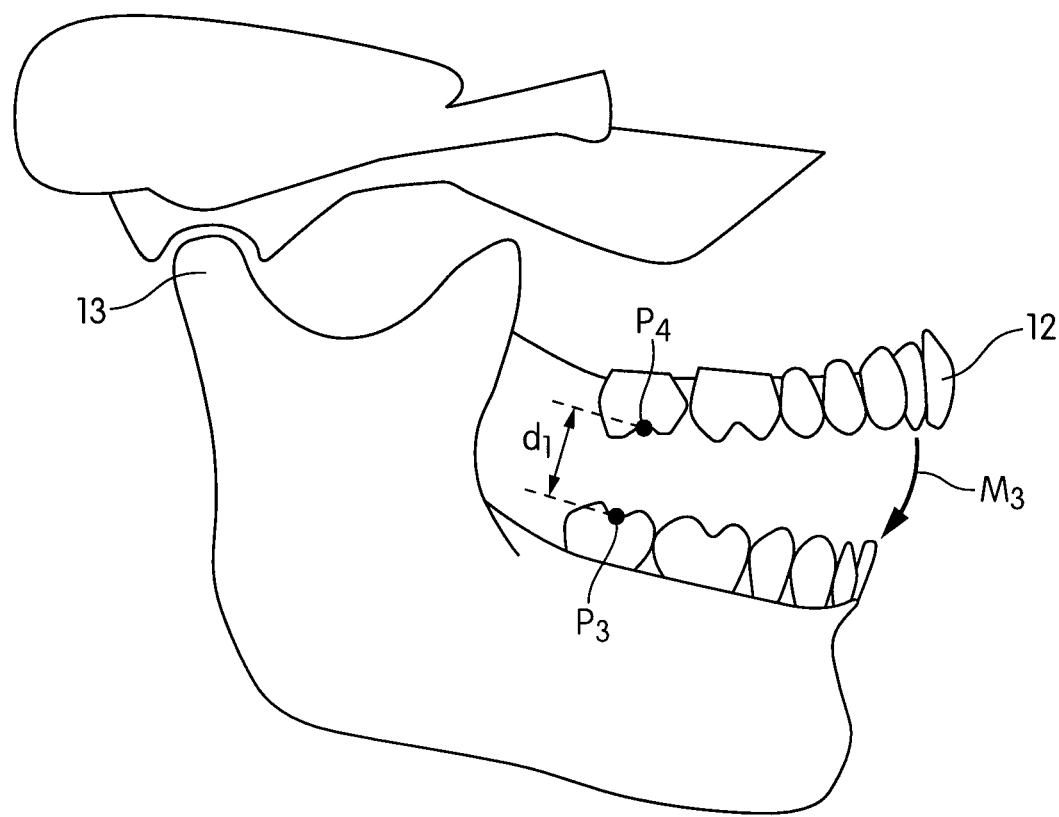
FIG. 10b is a side view of a jaw illustrating a second movement of a patient's oral cavity according to an exemplary embodiment of the present invention.

Moving points 21 may indicate points at which the displacements and/or maximum distances corresponding to a particular masticatory movement may be measured. For example, when the patient moves the jaw in a needed position (depending on which articulation parameter is being measured), an image for a jaw in a first position (e.g. closed jaw) may be recorded and another image for the jaw in a second position (e.g. moved jaw) may be obtained. For example, when the patient moves the lower jaw in a movement $M_4$ as shown in FIG. 9 moving point 21 moves from position 1 to position 2. The distance between positions 1 and 2 can therefore be obtained from the images. Moreover, when the lower jaw moves away from the upper jaw in a movement $M_3$ as shown in FIGS. 10a and 10b, a displacement $d_1$ between points $P_3$ and $P_4$ may then be identified and measured. Points $P_3$ and $P_4$, may be any points of interest and may not be limited to the molars alone. For example, they may define the contact points of the mandibular central incisors' incisal edge or the midline of the mandibular residual ridge. Said points may also be located in similar positions in humans and may therefore be determined by feature analysis/extraction.

In embodiments where predetermined artificial markers are not used, the fixed points 20 and/or moving points 21 may be determined through feature analysis of anatomical structures. Feature analysis may include defining features of the dentition that may be recognized and used in detecting larger structures. The features may include smaller points, edges, objects on an image and/or curves or boundaries defining different regions of an image. In an exemplary embodiment herein, feature analysis may include machine/deep learning methods wherein a computer may be trained to recognize fixed points 20 and moving points 21 based on previously classified images of faces. For example, starting with a plurality of images of human faces, a dental practitioner may label pixels of the images to be used for training by marking areas of interest e.g. the fixed points 20 and/or moving points 21. The marking of the training images may be done digitally e.g. by setting dots on the images corresponding to the points of interest. Using this set of labeled or classified images, a network architecture/deep neural network such as a convolutional neural network (CNN) may be built and fed with the labeled pictures allowing the network to "learn" from it such that the network may produce a network wiring that may classify new images on its own. After the training, the network may be given previously unseen images and the output, such as a location probability vector containing location probability values wherein the highest location probability values may define locations of the fixed 20 and/or moving points 21 may be obtained and corresponding feedback may be given such that the network may preferably operate on its own eventually to classify images without human help. The images used for training may also be derived from or otherwise based on ongoing patient treatments, past patient treatments, the results of patient treatments or otherwise treatment information.

After obtaining the fixed points 20 and/or moving points 21, the values of the articulator parameters may be obtained using geometrical distances and angles measured with the obtained fixed points 20 and/or moving points 21 as shown in Step S400. Some articulation parameters may be measured using just the fixed points 20 or single images while other articulation parameters may be obtained using the fixed points 20 and the moving points 21 or multiple images. For example, in determining the maximum displacement of displacement $d_1$ during movement $M_3$, there may be multiple images depicting multiple locations of the lower jaw. Images with the biggest difference regarding points of interest may be obtained and the Euclidean distance between those points may be calculated. Using an extracted or recognized point representing the location of the temporomandibular joint 23 along with the displacement $d_1$ and/or other fixed points 20 and moving points 21, Euclidean geometry employing the use of lines, angles and triangles or coordinates in space obtained from, for example, 3D reconstruction or images may be used to measure values of the articulation parameters. A computer system 100 may thus be programmed to carry out these steps repeatedly by means of an algorithm that combines the deep learning feature extraction or simpler object recognition methods such as gradient matching or template matching or the like with methods involving the measuring of relevant distances and angles.

Other systems and methods for dental measurements may include those taught in U.S. Pat. No. 8,126,726B2, entitled "System and method for facilitating automated dental measurements and diagnostics", by Matov et al, which is incorporated by reference herein in its entirety, as if set forth fully herein.

After obtaining the values for the articulation parameters, a virtual articulator may be filled with said values as shown in Step S500. The filled in virtual articulator may then be used to complete a treatment procedure, Step S600, such as in creating a restoration or analyzing the correct function of teeth 12 of the patient. Moreover, the obtained values may be transmitted, for example wirelessly, to a CAD/CAM software, wherein the values may be integrated and used for the calculation of a functionally proper proposal of a restoration or other dental or orthodontic appliance.

Further, the 3D reconstruction of the face 10 may be superimposed with an intraoral data record, such as a 3D measurement/scan of the intraoral cavity of the patient taken with an intraoral scanner, for example, in order to visualize the restoration or treatment planning and/or results of the treatment planning. The superimposition may be done by identifying common regions in both data such as teeth and overlaying the data together along the common regions.

Preferably the process S1000 may be completed in a short time period (e.g. a few seconds to 2 minutes) as compared to about 45 minutes in the use of a physical facebow and/or physical virtual articulator. Moreover, potentially higher precision may be achieved, and the process may also preferably drastically reduce the cost of articulation and user errors, leading to a higher application rates. In addition, the process may also be comfortable for patients resulting in a higher customer satisfaction with the dentist.

System for Determining Articulation Parameters

Figure 11:
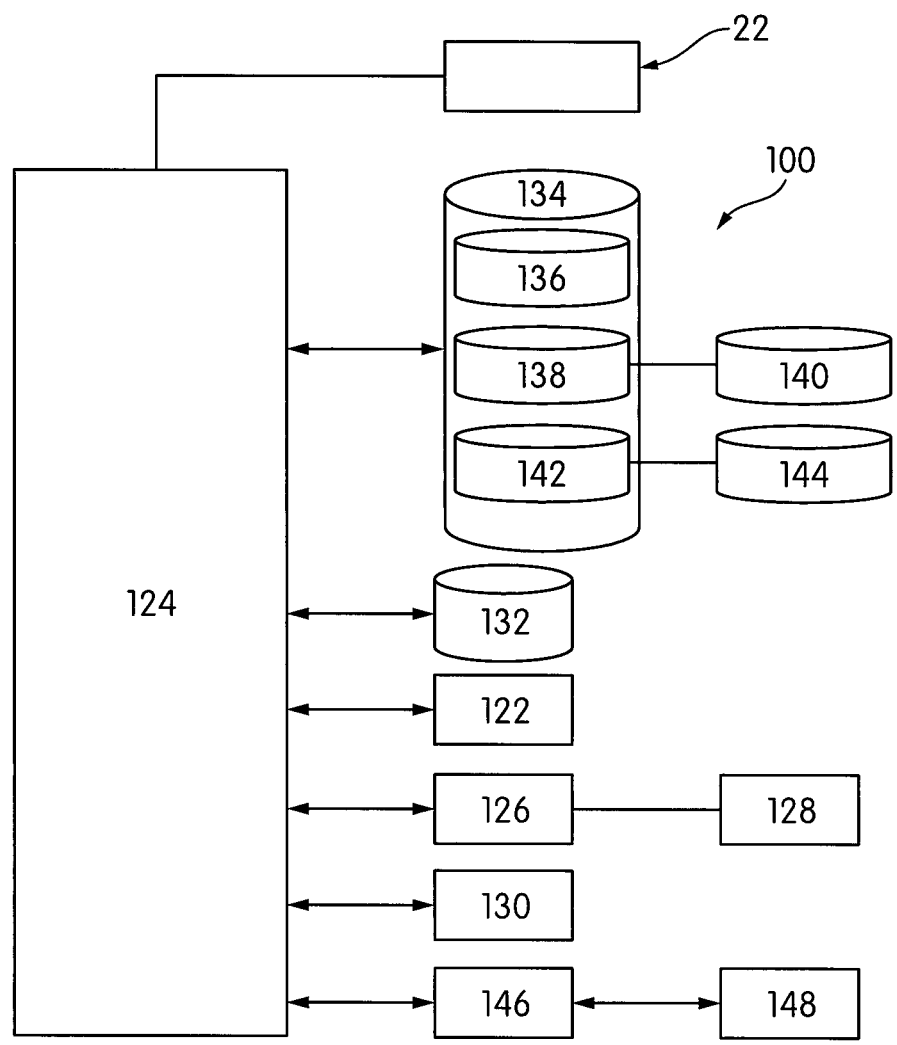
FIG. 11 is a block diagram showing a computer system according to an exemplary embodiment of the present invention.

Having described the system 1 of FIG. 9 reference will now be made to FIG. 11, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the disclosure using other computer systems and/or architectures.

In one example embodiment, the computer system may include a camera system 22 which may operate under one of several depth sensing principles including, for example, (i) structural light, (ii) Time of Flight (ToF) and/or (iii) stereoscopic principles. For cameras employing structural light, a light source may be used to project a known pattern onto the patient or patient's head, and a receiver may detect the distortion of the reflected pattern to calculate depth map based on geometry. For cameras employing Time of Flight (ToF) principles, a light source may send out a pulse, and a sensor may detect a reflection of the pulse from the patient in order to record it's time of flight. Knowing that and the constant speed of light, the system may calculate how far away the points on the patient's head. Alternatively, a modulated light source may be send and a phase change of light reflected from the patient may be detected. For cameras employing stereoscopic principles, multiple cameras may be placed at different positions to capture multiple images of the patient's head, and a depth map may be calculated based on geometry. This depth information may be used to track the patient's head during treatment.

The computer system 100 may also include at least one computer processor 122, user interface 126 and input unit 130. The input unit 130 in one exemplary embodiment may be used by the dentist along with a display unit 128 such as a monitor to send instructions or requests about the capturing of images of the face, the reconstruction of 3D images of the face 10, the determination of fixed points 20 and moving points 21 and/or the calculation of articulator values. They may also be used for treatment planning including for example, the creation of a restoration. In another exemplary embodiment herein, the input unit 130 is a finger or stylus to be used on a touchscreen interface (not shown). The input unit 130 may alternatively be a gesture/voice recognition device, a trackball, a mouse or other input device such as a keyboard or stylus. In one example, the display unit 128, the input unit 130, and the computer processor 122 may collectively form the user interface 126.

The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive a request for automatically capturing images of the face, automatically storing the images in a database, automatically reconstructing a 3D model of the face 10, automatically determining fixed points 20 and moving points 21, automatically calculating and filling in articulator parameters and/or automatically producing a treatment plan, restoration or analysis of the functioning of teeth 12. The processor 122 may then load said instructions and execute the loaded instructions such as using a database or artificial intelligence (AI) to obtain treatments for display.

One or more steps/procedures for determining articulator parameters may be stored on a non-transitory storage device in the form of computer-readable program instructions. To execute a procedure, the processor 122 loads the appropriate instructions, as stored on a storage device, into memory and then executes the loaded instructions.

The computer system 100 may further comprise a main memory 132, which may be a random access memory ("RAM") and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or a wireless interface), a communications port (e.g., a Universal Serial Bus ("USB") port or a FireWire® port), a Personal Computer Memory Card International Association ("PCMCIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described hereinafter.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the system for determining articulator parameters, to perform all or some of the methods described herein.

In another example embodiment, the computer system 100 may be a mobile device such as a smartphone having an application that may be engaged by a user to propose and visualize dental and orthodontic treatments.

Implementation of other hardware arrangement so as to perform the functions described herein will be apparent to persons skilled in the relevant art(s) in view of this description.

What is claimed is:

1. A method for determining articulation parameters, the method comprising the steps of:
receiving images of a patient's face;
determining defined fixed and/or moving points in the images of the patient's face, for calculating articulation parameters, using a trained neural network, the trained neural network being trained based on a dataset of labelled training images to identify points of interest corresponding to one or more fixed and/or moving training points by mapping the one or more fixed and/or moving training points in the training images to one or more highest location probability values of a location probability vector, the one or more highest location probability values being indicative of a location of the fixed and/or moving training points;

computing a set of geometrical distances and angles between the determined fixed and/or moving points;

calculating, responsive to the determining step, the articulator parameters based on the geometrical distances and/or angles measured using the determined fixed and/or moving points; and, using the calculated articulator parameters to fill a virtual articulator with articulation values.

2. The method according to claim 1, wherein the articulator parameters are chosen from the group consisting of (i) Sides of a Bonwill triangle, (ii) Intercondylar distance, (iii) Balkwill angle, (iv) Sagittal condylar path inclination, (v) Bennett angle, (vi) Initial Bennett movement and (vii) Curve of Spee.

3. The method according to claim 1, further comprising reconstructing a 3D model of a face of the patient from the received images.

4. The method according to claim 1, further comprising superimposing a scan of the intraoral cavity of the patient on the 3D model.

5. The method according to claim 1, wherein the fixed points include a location of a temporomandibular joint.

6. The method according to claim 1, further comprising analyzing the functioning of teeth based on the articulator parameters.

7. The method according to claim 1, further comprising producing a restoration or a treatment plan based on the articulator parameters.

8. The method according to claim 1, wherein the trained neural network is a convolutional neural network.

9. A system for determining articulation parameters, the system comprising at least one processor configured to perform the steps of:

receiving images of a patient's face;

determining defined fixed and/or moving points in the images of the patient's face, for calculating articulation parameters, using a trained neural network, the trained neural network being trained based on a dataset of labelled training images to identify points of interest corresponding to one or more fixed and/or moving training points by mapping the one or more fixed and/or moving training points in the training images to one or more highest location probability values of a location probability vector, the one or more highest location probability values being indicative of a location of the fixed and/or moving training points;

computing a set of geometrical distances and angles between the determined fixed and/or moving points;

calculating, responsive to the determining step, the articulator parameters based on the geometrical distances and/or angles measured using the determined fixed and/or moving points; and, using the calculated articulator parameters to fill a virtual articulator with articulation values.

10. The system according to claim 9, wherein the processor is further configured to choose the articulator parameters from the group consisting of (i) Sides of a Bonwill triangle, (ii) Intercondylar distance, (iii) Balkwill angle, (iv) Sagittal condylar path inclination, (v) Bennett angle, (vi) Initial Bennett movement and (vii) Curve of Spee.

11. The system according to claim 9, wherein the processor is further configured to reconstruct a 3D model of a face of the patient from the received images.

12. The system according to claim 9, wherein the processor is further configured to superimpose a scan of the intraoral cavity of the patient on the 3D model.

13. The system according to claim 9, wherein the fixed points include a location of a temporomandibular joint.

14. The system according to claim 9, wherein the processor is further configured to produce a restoration or a treatment plan based on the articulator parameters.

15. A non-transitory computer-readable storage medium storing a program which, when executed by a computer system, causes the computer system to perform a procedure comprising:

receiving images of a patient's face;

determining defined fixed and/or moving points in the images of the patient's face, for calculating articulation parameters, using a trained neural network, the trained neural network being trained based on a dataset of labelled training images to identify points of interest corresponding to one or more fixed and/or moving training points by mapping the one or more fixed and/or moving training points in the training images to one or more highest location probability values of a location probability vector, the one or more highest location probability values being indicative of a location of the fixed and/or moving training points;

computing a set of geometrical distances and angles between the determined fixed and/or moving points;

calculating, responsive to the determining step, the articulator parameters based on the geometrical distances and/or angles measured using the determined fixed and/or moving points; and, using the calculated articulator parameters to fill a virtual articulator with articulation value.

\* \* \* \* \*